(12) United States Patent  (10) Patent No.: US 7,141,708 B2
Marsella et al.  (45) Date of Patent: Nov. 28, 2006

(54) HOLLOW PELLET SUITABLE AS CARRIER OF CATALYSTS FOR SELECTIVE EXOTHERMIC REACTIONS

(75) Inventors: Andrea Marsella, Paese (IT); Sandro Vidotto, Pordenone (IT); Barbara Cremaschi, Mestre (IT)

(73) Assignee: Ineos Vinyls UK Ltd., Runcorn (GB)

( * ) Notice: Subject to any disclaimer, the term of this patent is extended or adjusted under 35 U.S.C. 154(b) by 276 days.

(21) Appl. No.: 10/630,551

(22) Filed: Jul. 29, 2003

(65) Prior Publication Data

US 2005/0075246 A1 Apr. 7, 2005

(30) Foreign Application Priority Data

Jul. 31, 2002 (EP) ................... 02255354

(51) Int. Cl.
*C07C 17/15* (2006.01)
(52) U.S. Cl. .................. 570/245; 502/527.17
(58) Field of Classification Search ........... 570/245; 502/302–304, 326, 328, 330, 331, 337, 344, 502/345, 342, 527.17
See application file for complete search history.

(56) References Cited

U.S. PATENT DOCUMENTS

| | | | |
|---|---|---|---|
| 4,366,093 A | 12/1982 | Shiozaki et al. | 252/477 R |
| 4,382,021 A | 5/1983 | Laurer et al. | 252/441 |
| 4,740,644 A | 4/1988 | Eichhorn et al. | 570/245 |
| 5,166,120 A | 11/1992 | Deller et al. | 502/225 |
| 5,841,009 A * | 11/1998 | Carmello et al. | 570/245 |
| 6,465,701 B1 * | 10/2002 | Marsella et al. | 570/245 |

FOREIGN PATENT DOCUMENTS

| | | |
|---|---|---|
| EP | 0 054 674 | 6/1982 |
| EP | 1 053 789 A1 | 11/2000 |
| WO | WO 95/18895 | 7/1995 |
| WO | WO 96/40431 | 12/1996 |

* cited by examiner

*Primary Examiner*—Cam N. Nguyen
(74) *Attorney, Agent, or Firm*—Woodcock Washburn LLP

(57) ABSTRACT

A hollow catalyst pellet for use in selective gas phase exothermic reactions in a tubular fixed bed reactor, having a parallelogram shaped external cross-section.

34 Claims, 8 Drawing Sheets

HOLLOW PELLET SUITABLE AS CARRIER OF CATALYSTS FOR SELECTIVE EXOTHERMIC REACTIONS

This invention relates to novel catalyst pellets for exothermic reactions in tube reactors using a fixed bed catalyst.

The exothermic reactions are not particularly limited. Preferably the catalyst pellets are used for selective chlorination and/or oxychlorination of alkenes or alkanes and selective oxidation of alkenes. For sake of clarity, the present invention is described particularly with reference to catalyst pellets for the oxychlorination of ethylene to 1,2-dichloroethane.

The vapour-phase oxychlorination of ethylene to 1,2-dichloroethane using a fixed bed reactor containing a supported catalyst, usually a supported copper catalyst, is widely used commercially, for example as a part of the process for producing vinyl chloride monomer. The industry is constantly seeking to improve the efficiency of the process, and much work has been reported on the effects of different catalysts on the process. Thus, both the composition and physical presentation of the catalyst have been studied. The present invention is concerned in particular with the physical shape of the catalyst.

Over the last few years some improvements have been reported in catalytic performance obtained by suitable modification of the shape and/or size of catalysts in pellet form. Such characteristics affect some of the most important properties of the catalytic bed in fixed bed reactors, such as: i) the resistance to the reactant flux (pressure drop), which determines the maximum possible flow through the reactor; ii) the efficiency of heat exchange, which allows the removal of heat from the highly exothermic oxychlorination reaction; and iii) the effectiveness of the pellet as far as the diffusion of reactants and reaction products inside the pellets is concerned.

A low pressure drop favours the flow through the catalytic bed, and therefore allows the increase of the productivity of industrial reactors. On the other hand the increase of the pressure drop with the catalyst lifetime is a common reason for replacing the catalyst in industrial reactors, an initial low pressure drop allows a larger range of pressure drop increase and, consequently, a longer use of the catalyst before its replacing.

Starting from the usual catalysts, shaped as spheres or solid cylinders, a lower pressure drop through the catalytic bed has been obtained by developing catalysts based on hollow pellets shaped with a columnar configuration and a circular or multilobed cross-section, which give rise to catalytic beds with higher void fractions and, consequently, with lower pressure drop.

Catalysts of this type, for use in oxychlorination reactions, have been described for example in the following patents or patent applications.

U.S. Pat. No. 4,366,093 reports a hollowed cylindrical catalyst having an outer diameter $D_e$ in the range 3–6 mm, an internal diameter $D_i \geq 1$ mm, a wall thickness of at most 1,5 mm and a length L in the range 3–6 mm.

U.S. Pat. No. 4,382,021 and EP 54674 describe a hollowed cylinder catalyst having the size $D_e$=5–12 mm, $D_i$=3–8 mm and L=3–12 mm.

U.S. Pat. No. 4,740,644 claims a new method for preparing hollowed catalysts and exemplifies catalysts with $D_e$=5 mm, $D_i$=1.8 mm and L=5 mm.

In U.S. Pat. No. 5,166,120 a catalyst prepared by extrusion, shaped as a hollowed cylinder with $D_e$=4–6 mm, $D_i$=1–2 mm and L=1.7–3.75, is described.

Hollow cylindrical pellets have a S/V (geometric surface to volume ratio) higher than spheres and solid cylinders, and this property, together with a higher void fraction of catalytic bed, gives a more efficient heat exchange. Thus, better temperature control along the catalytic bed and reduced hot spot temperatures are obtained: in this way a longer catalyst life is achieved and the reaction results in a reduced formation of chlorinated by-products and combustion products.

A further benefit of hollowed cylindrical pellets, due to their higher geometric surface combined with a lower wall thickness, is their higher effectiveness, because the reaction takes place only in a thin external layer. By using hollowed cylindrical pellets also the formation of carbonaceous deposits inside the core of the pellet, responsible for pellet breakage and pressure drop increase during the industrial run, is reduced; consequently, an increase of catalyst life can be obtained.

In order to obtain the above described advantages a hollowed pellet must be designed carefully, otherwise several disadvantages become evident. For example, if the $D_i/D_e$ ratio of a hollowed cylinder is greater than a certain value, the pellet becomes too fragile, without further advantage in terms of effectiveness. Moreover, the apparent bulk density of the catalyst decreases, resulting in a lower conversion per unit volume of catalyst bed due to the lower total active phase content in the reactor. This last effect can affect also the catalyst life, because the catalyst tends to lose active phase compounds in the reaction environment. A solution to this problem could be an increase of the active phase concentration of fresh catalyst, because an excess of active phase compounds, even if not contributing directly to the catalyst activity, can act as a reservoir, increasing the catalyst life. However the active phase concentration can not be increased over a certain extent, because the consequent loss of the catalyst surface area causes a loss of activity.

A further improvement for pellets having a hollowed cylinder shape is described in the patent application EP 1053789 in the name of the Applicant, wherein a particular hollow cylinder size of the pellet is described.

Catalyst having a shape different from a hollowed cylinder have been also investigated. WO 96/40431 describes a catalyst for ethylene oxychlorination having a partially hollow cylindrical shape with internal reinforcing vanes. The cross-section is shaped like a "spoked wheel", the outer diameter $D_e$ is greater than 6.5 mm, the wall thickness is in the range of 0.1 to 0.3 times $D_e$ and the length is in the range of 0.5 to 5 times $D_e$.

EP 687331 discloses an ethylene oxychlorination catalyst in granular form, consisting of copper chloride supported on an alumina carrier, having a columnar configuration with a trilobed cross-section provided with three through-bores coaxial with said lobes. The axes of the lobes are substantially parallel to each other and substantially equidistant from each other.

With these particular configurations of said patents, more complex than the hollowed cylinder, it was tried to improve one or more of the relevant features described above, i.e.: i) reduction of the pressure drop, ii) increase of the S/V factor, iii) reduction of the pellet wall thickness. However these configurations show low bulk density and/or low mechanical resistance, which can reduce or, even, overcome the achieved improvements in terms of reactor productivity and catalysts lifetime.

The above remarks make clear that, producing pellet shaped oxychlorination catalysts, it must be taken into account that every change capable of giving rise to some improvement in catalytic performance can also cause unwanted detrimental effects, especially if the changes are not balanced carefully by the simultaneous modification of other characteristics. As a conclusion, in order to obtain an excellent oxychlorination catalyst it is not sufficient to optimise a single characteristic: all the properties must be carefully balanced as a whole. It was felt the need to have available catalyst pellets which show a good combination of the above described requirements without the disadvantages reported above: i) lower pressure drop of the catalytic bed due to the particular shape of the pellet which increases the void fraction of the catalytic bed, ii) better heat exchange, iii) good effectiveness, iv) good mechanical resistance of the pellets in order to have pellets not too fragile, v) high bulk density guaranteeing a high total active phase content of the reactor. A good combination of the above features would allow to obtain in the oxychlorination reaction the following advantages: i) improved selectivity, ii) good conversion, iii) longer catalyst lifetime.

An object of the present invention is therefore a catalyst pellet for selective gas phase exothermic reactions in a tubular fixed bed reactor, wherein said catalyst pellet has:

I. an uniform cross-section or, if not uniform, with a deviation from the average cross-section area lower than 30%;
II. a parallelogram cross-section, preferably a rhomboidal or square cross-section;
III. one or more through-bores:
  A. with axes which are parallel to each other and to the axis of the pellet or, if not parallel, with a deviation from parallel line lower than 20%;
  B. with uniform section or, if not uniform, with a deviation from the average cross-section lower than 30%, particularly with one of the following embodiments:
    1. with one bore having the same shape of the cross-section of the pellet or, optionally, with two or more bores obtained by introducing internal reinforcing vanes in said one bore;
    2. with two or more bores having a rounded shape, particularly a circular or elliptical shape and, if four or more bores are present, with different distances between the centres of the non-adjacent couples of bores.

Some very schematic examples are reported in FIG. 1 to illustrate, but not to limit, the present invention. The Figure shows three possible embodiments based on the same external rhomboidal cross-section and with four bores. In example A the four bores have been obtained from one bore having the same shape of the external contour of the pellet cross introducing two reinforcing vanes connecting the edges of the rhomb. In example B the four bores have been obtained from one bore having the same shape of the cross-section of the pellet introducing two reinforcing vanes connecting the sides of the rhomb. In example A the four bores are elliptical.

The sides of the external cross-section of the pellet may also be curved and its corners may be rounded in order to confer an improved mechanical strength, to reduce the abrasion and to favour the manufacture. The ratio between the area of the cross-section of the pellet, including the cross-section of the bores, and the area of the parallelogram circumscribing the external contour of the pellet cross-section is higher than 0.75, preferably higher than 0.85. The curves may be convex or concave or both. The whole external contour of the pellet cross section may be convex or the curves corresponding to the sides of the external contour of the pellet cross-section may be concave and the curves corresponding to the edges of the external contour of the pellet cross-section may be convex. In the embodiment containing bores with circular or elliptical cross-section, the convex curve corresponding to the edges and the concave curve corresponding to the sides of the cross-section are preferred.

The pellets with one bore having the same shape of the cross-section of the pellet or, optionally, with two or more bores obtained by introducing internal reinforcing vanes in said one bore may have the sides and/or the corners of the contour of the bores cross-section rounded in such a way that the ratio between the area of the cross-section of the bores and the area of the parallelogram circumscribing the external contour of the bores cross-section is higher than 0.75, preferably higher than 0.85. The reinforcing vanes of the pellets having one bore with the same shape of the external contour of the pellet cross-section preferably are disposed to connect the opposite edges or the opposite sides of the external contour of the bore cross-section.

When more than one bore is present in the pellet, they can have the same size or different size, preferably the bores have the same size.

The catalyst pellets of the present invention have the following size: 4 mm<$P_1$<15 mm, 4 mm<$P_2$<15 mm, 0.5 mm<$P_3$<4 mm, 3 mm<$P_4$<15 mm, wherein $P_1$ is the main diagonal of the parallelogram, $P_2$ is the secondary diagonal of the parallelogram, $P_3$ is the maximum wall thickness, $P_4$ is the length of the parallelogram. It is meant for wall thickness the minimum distance between a given point of the bore wall and the external wall of the pellet or the wall of an adjacent bore. When the bores have circular shape the diameter is in the range of 0.7 to 3 mm.

The catalyst pellets of the present invention have preferably the following size: 4 mm<$P_1$<9 mm, 4 mm<$P_2$<9 mm, 0.7 mm<$P_3$<2 mm, 4 mm<$P_4$<8 mm, wherein $P_1$, $P_2$, $P_3$ and $P_4$ have the meaning above indicated.

Some examples are shown in FIGS. 2–4, which represent preferred embodiments of the invention. In FIG. 2 a pellet having a rhomboidal cross-section with one reinforcing vane and two bores is reported. In FIG. 3 a pellet having a square cross-section with two reinforcing vanes and four bores is reported. Alternatively to the square cross-section of FIG. 3 a pellet with a rectangular cross-section is suitable for use. In FIG. 4 a pellet having a rhomboidal cross-section with four circular bores is reported.

With reference to FIG. 2, the catalyst pellet of the present invention has the following size: 4 mm<$R_1$<15 mm, 4 mm<$R_2$<15 mm, 0.5 mm<$R_3$<3 mm, 3 mm<$R_4$<15 mm, wherein $R_1$ is the longest size of the cross-section, $R_2$ is the shortest size of the cross-section, $R_3$ is the largest wall thickness of the bores, $R_4$ is the length. Preferably: 4 mm<$R_1$<9 mm, 4 mm<$R_2$<9 mm, 0.7 mm<$R_3$<2 mm, 4 mm<$R_4$<8 mm.

With reference to FIG. 3, the catalyst pellet of the present invention has the following size: 3 mm<$Q_1$<10.5 mm, 0.5 mm<$Q_3$<3 mm, 3 mm<$Q_4$<15 mm, wherein $Q_1$ is the side of the square, $Q_3$ is the wall thickness, $Q_4$ is the length. Preferably: 4 mm<$Q_1$<9 mm, 0.7 mm<$Q_3$<2 mm, 3 mm<$Q_4$<8 mm.

With reference to FIG. 4, the catalyst pellet of the present invention has the following size: 4 mm<$T_1$<15 mm, 4 mm<$T_2$<15 mm, 0.5 mm<$T_3$<3 mm, 3 mm<$T_4$<15 mm, wherein $T_1$ is the longest size of the cross-section, $T_2$ is the shortest size of the cross-section, $T_3$ is the largest wall thickness of the bores, $T_4$ is the length. The diameter of the bores is comprised between 0.7 and 3 mm. Preferably: 4 mm<$T_1$<9 mm, 4 mm<$T_2$<9 mm, 0.7 mm<$T_3$<2 mm, 3 mm<$T_4$<8 mm.

Further examples are shown in FIGS. 5–7, which represent preferred embodiments of the invention with curved external surfaces. In FIG. 5 the same pellet as FIG. 2, but with convex external surfaces is reported. In FIG. 6 the same pellet as FIG. 3, but with convex external surfaces is reported. In FIG. 7 the same pellet as FIG. 4, but with concave external surfaces is reported.

The exothermic reactions in which the pellets of the present invention can be applied are not particularly limited. Preferably they are used for selective chlorination and/or oxychlorination of alkenes, e.g. ethylene, or alkanes e.g. methane and ethane; selective oxidation of alkenes, e.g. ethylene and propylene. For example it can be mentioned the reaction of ethylene with chlorine to give 1,2-dichloroethane, the reaction of ethylene with hydrogen chloride and air or oxygen to give 1,2-dichloroethane, the reaction of methane with chlorine, the selective oxidation of ethylene or propylene, etc.

Preferably the catalyst pellets of the invention are used in the oxychlorination of hydrocarbons, especially the vapour phase oxychlorination of ethylene to EDC. The carrier material of the catalyst of the present invention may be any of the materials known for producing supported catalysts. Examples include silica, pumice, diatomaceous earth, alumina and other aluminium hydroxo compounds such as boehmite and bayerite. For the oxychlorination reaction the preferred carrier materials are γ-alumina or other transitional aluminas and boehmite, the latter normally being pre-heated to convert it into alumina. The carrier material suitably has a surface area (BET) of 50–350 m2/g. The active material supported on the carrier contains copper in an amount of 1–12 wt % based on the weight of the dry catalyst. The copper will normally be deposited on the carrier in the form of a salt, especially as halide and preferably as cupric chloride. The copper may be used in combination with other metal ions in order to have the desired selectivity and conversion. Such other metals include, for example, alkali metals (such as Li, Na, K, Ru, Cs), alkaline-earth metals (such as Mg, Ca, Ba), group IIB metals (such as Zn and Cd) and lanthanides (such as La, Ce and so on) or a suitable combination of them. These additional metal ions can be added as salts or oxides, the total amount of additives suitably being in the range 0–15 wt %. They can be added together with the copper or alternatively one or more of them (even all) after or even before the copper. In the last case their addition can be followed by an intermediate heat treatment. Preferred alkali metals are Li and K and Cs and they are preferably added as chlorides, each of them in the range 0–8 wt %. The preferred alkaline-earth metal is Mg, added in the range 0–6 wt %. Preferred lanthanides are La and Ce, each of them added in the range 0–12 wt %. The addition of the active components can be accomplished by methods well known by those of skill in catalyst preparation. Here can be mentioned, for example, dry impregnation, incipient wetness impregnation or dipping, using a suitable solution of compounds to be added, for example an aqueous solution, optionally containing also acids such as HCl. The addition of the active components can be made partially or totally before or after the formation of the hollow pellets. Preferably the catalysts are prepared by impregnation of the already formed carrier. The shaping of the carrier or the catalyst may be performed by well known methods such as tabletting and extrusion. These operations are performed in the usual manner, optionally using additives such as lubricants and/or binders. Preferably the shaped pellets are obtained by tabletting, in order to have a more uniform pellet size, density and higher mechanical resistance. The operations include customary thermal treatments, such as calcination of the carrier at 500–1100 K, preferably at 750–950 K, if the active part is added to the carrier after the shaping procedure and drying at 330–600 K after addition of the active components.

The catalytically active material for selective oxidation of alkenes contains silver. The catalytically active material may preferably also comprise at least one of alkali metals, alkaline earth metals, group IIB metals, group VIIB metals, group VIIIB metals and lanthanides in a total amount preferably up to 5 wt %. Preferably the alkali metal is cesium, the alkaline earth is barium.

The catalyst for the oxychlorination of alkanes contains preferably copper and/or Ni and an alkali metal for example in the atomic ratio 2:8. The alkaly metal are preferably potassium or lithium or cesium. The catalytically active material may preferably also comprise at least one of alkaline earth metals, group IIB metals and lanthanides. Preferably the alkaline earth is magnesium and the lanthanide are lanthanum or cerium.

For the selective chlorination of alkenes and alkanes, the well known active components of the catalysts are used, for example alkali metals, alkaline earth metals, group IIB metals and lanthanides in a total amount preferably up to 30 wt % of the layer.

The carriers for the above active components of the catalysts of the above reactions are preferably aluminum hydroxides, aluminum oxide-hydroxides, alumina, silica, zirconia, titania, magnesia, pumice, diatomaceous earth zeolites or their mixtures or mixed compounds. Depending on the reaction the carriers may have high or low surface area.

In addition to the exothermic reactions, the pellets of the present invention can be used also for endothermic reactions with advantages similar to those achieved in selective exothermic reactions.

The following examples refer to the oxychlorination reaction of ethylene to 1,2-diochloroethane, taken as representative of selective gas phase exothermic reactions. Such examples are given for illustrative purposes and do not limit the scope of the invention.

EXAMPLES

DRAWINGS

The accompanying drawings have the purpose to illustrate, but not to limit, the invention. FIG. 1 shows three possible embodiments based on the same external rhomboedrical cross-section and with four bores. In example A the four bores have been obtained from one bore having the same shape of the cross-section of the pellet introducing two reinforcing vanes connecting the edges of the rhomb. In example B the four bores have been obtained from one bore having the same shape of the cross-section of the pellet introducing two reinforcing vanes connecting the sides of the rhomb. In example A the four bores are circular.

EXPERIMENTAL EQUIPMENT

Figure 8:
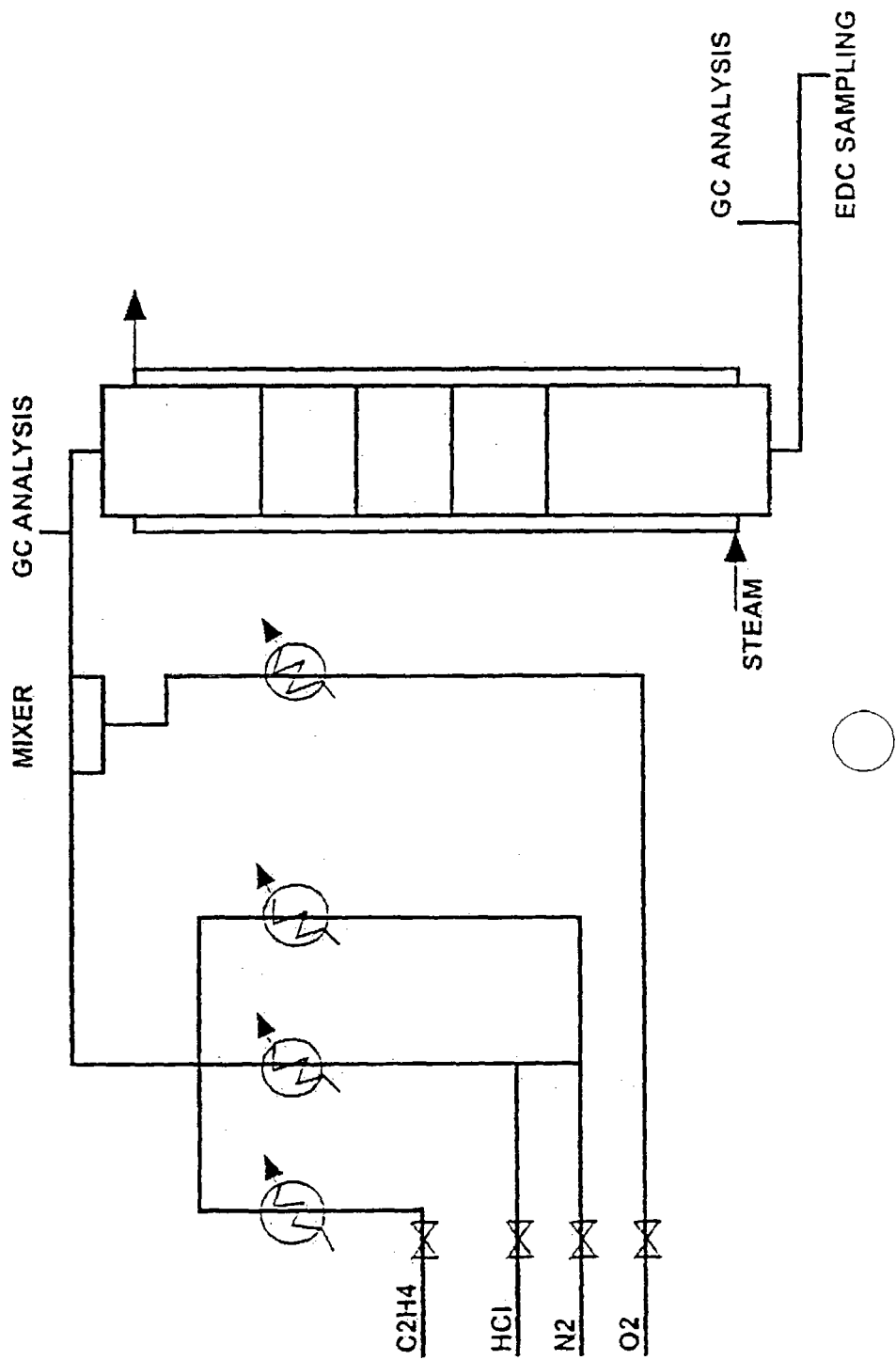
FIG. 8 is a schematic illustration, not to scale, of an exemplary pilot plant and reactor used for catalytic activity testing.

The choice of the method used for catalytic activity testing is very important, because the differences in term of conversion and selectivity to different products exhibited by different catalysts are usually small, but of great importance in 1,2-dichloroethane production in the common industrial large scale. The only way to obtain results which are truly representative of the industrial reactor is to perform the test using a tube with the same size as an industrial one and to adopt the same conditions (temperature, pressure, feed composition, flow and so on) as those used in the industrial reactor. The data reported below were obtained in a pilot plant using a tube having the same size as a typical industrial one and under a variety of different conditions covering those encountered during a typical industrial run. The reactor used (see FIG. 8) was a nickel tube 8 m long with an internal diameter of 27.75 mm. An external jacket with circulating steam was used to control the temperature profile. The reactor was equipped with a thermowell having an external diameter of 6 mm, containing 12 thermocouples to record the temperature profile during the tests. Two on-line gaschromatographs were used at the inlet and at the outlet of the reactor to control the reaction. The 1,2-dichloroethane was collected in a vessel containing isopropyl alcohol at about 0° C. and then analysed. This technique allows also the collection of the low boiling and the water soluble compounds (chloroethanol, chloral, etc.) as well as the unreacted HCl. The reactor feed was: 5200 Nl/h of $C_2H_4$, 600 Nl/h of $O_2$, 2.300 Nl/h of HCl, 1000 Nl/h of $N_2$. The oxygen was 6.5% vol (the flammability limit at 210° C. and at 6 bar is ca. 8%). The pressure at the inlet of the reactor was 6 bar, and the temperature of the coolant was 220° C.

Catalysts

Figure 1:
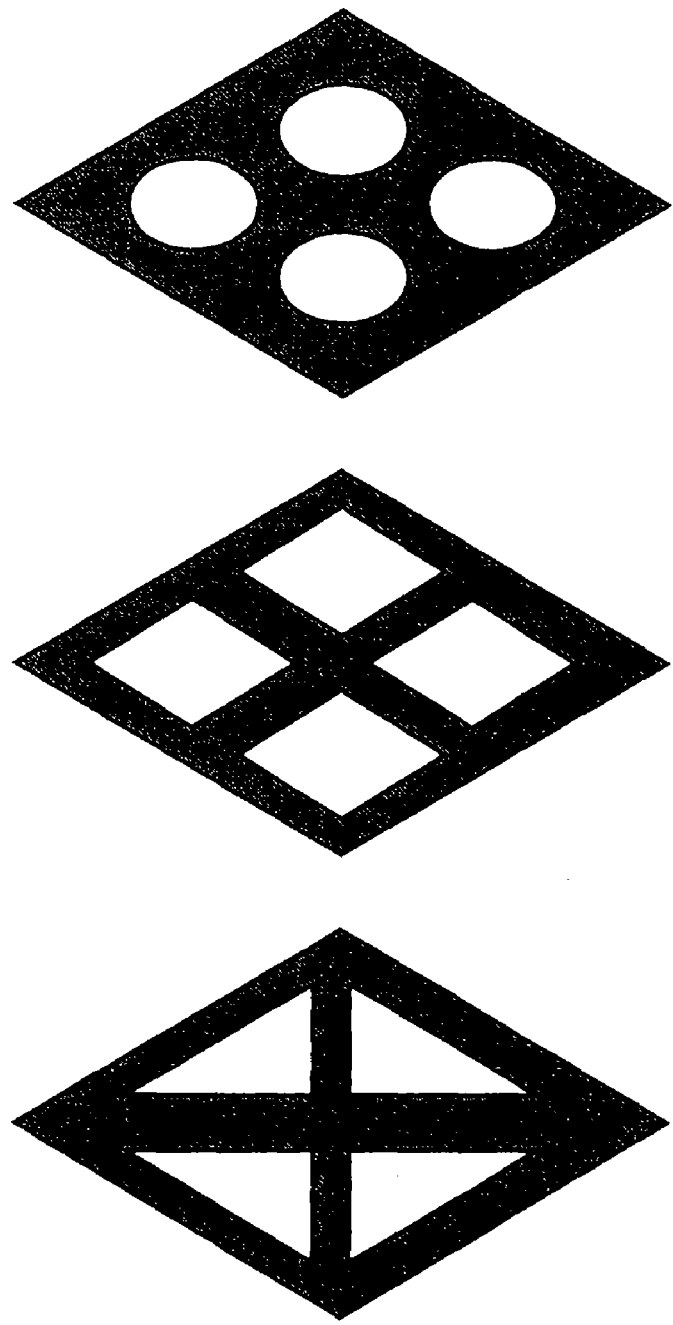
Figure 2:
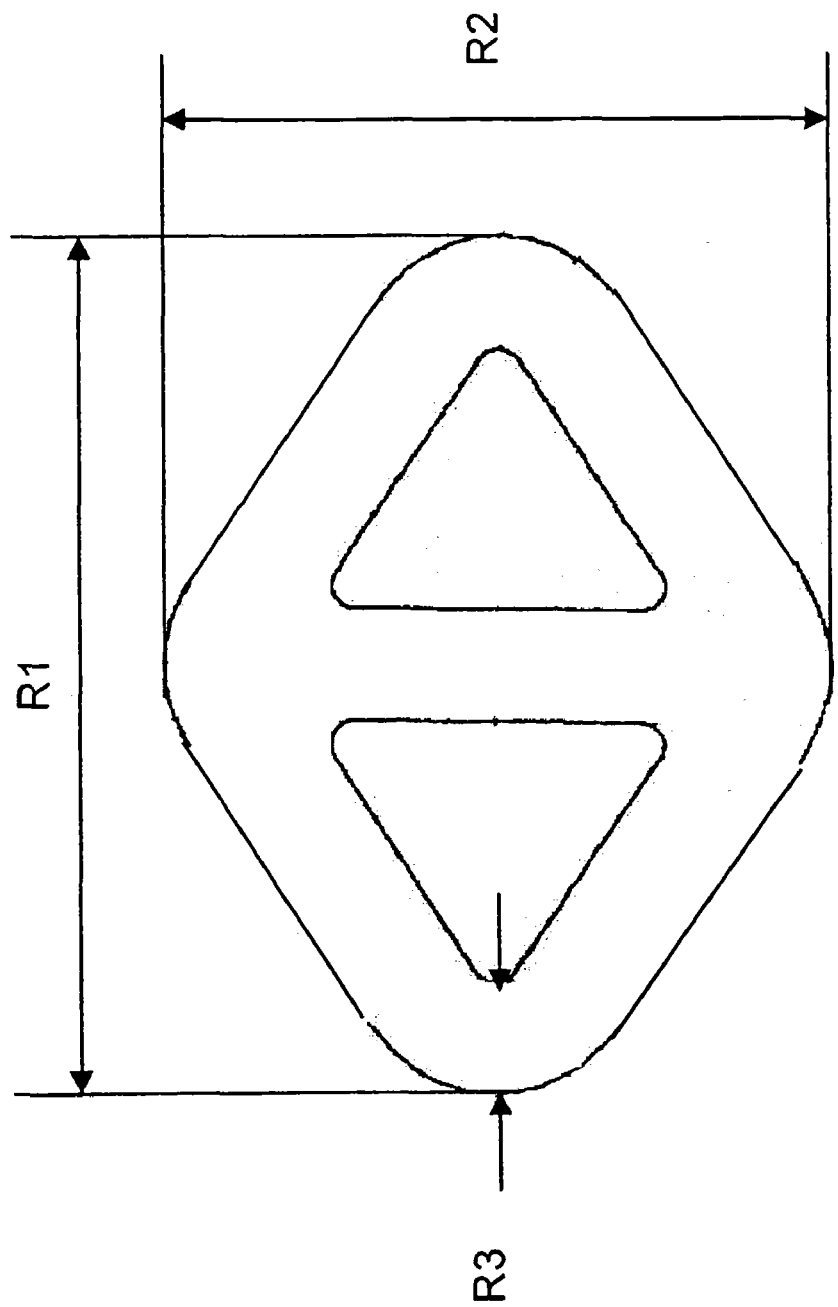
FIG. 2 is a schematic illustration, not to scale, of a catalyst pellet having a rhomboidal cross-section with one reinforcing vane and two bores.
Figure 3:
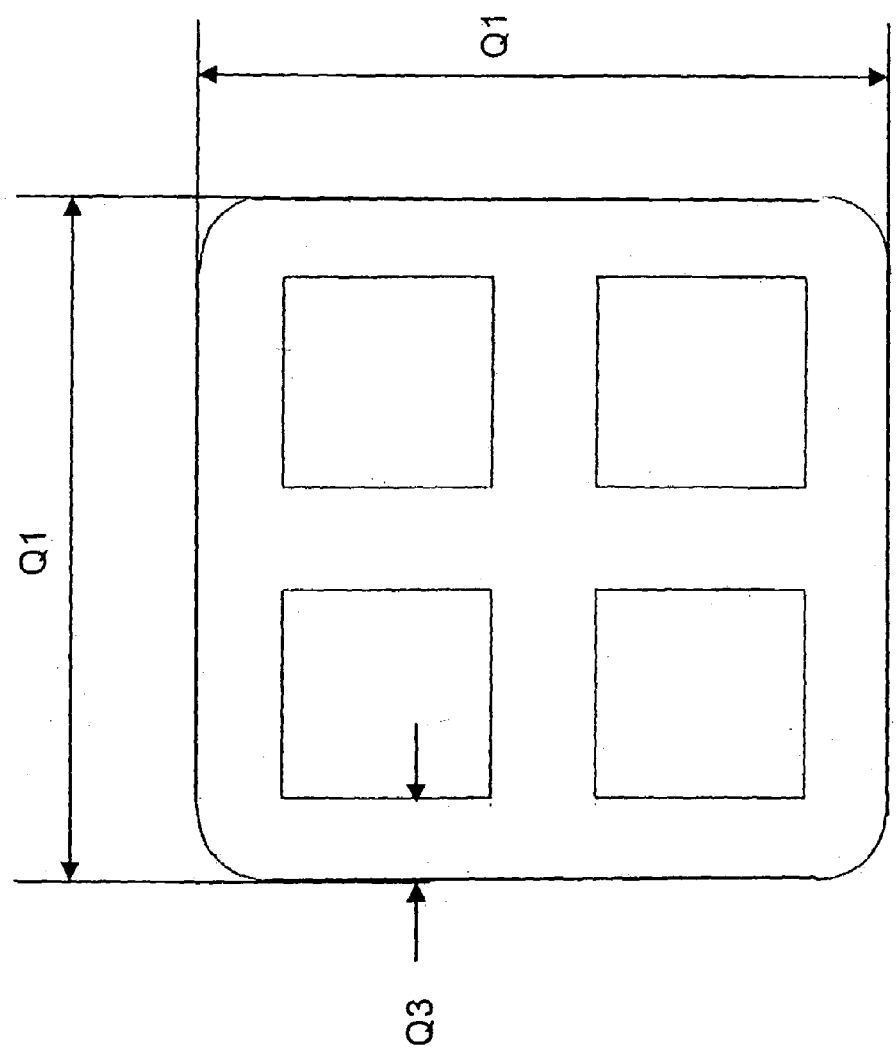
FIG. 3 is a schematic illustration, not to scale, of a catalyst pellet having a square cross-section with two reinforcing vanes and four bores.
Figure 4:
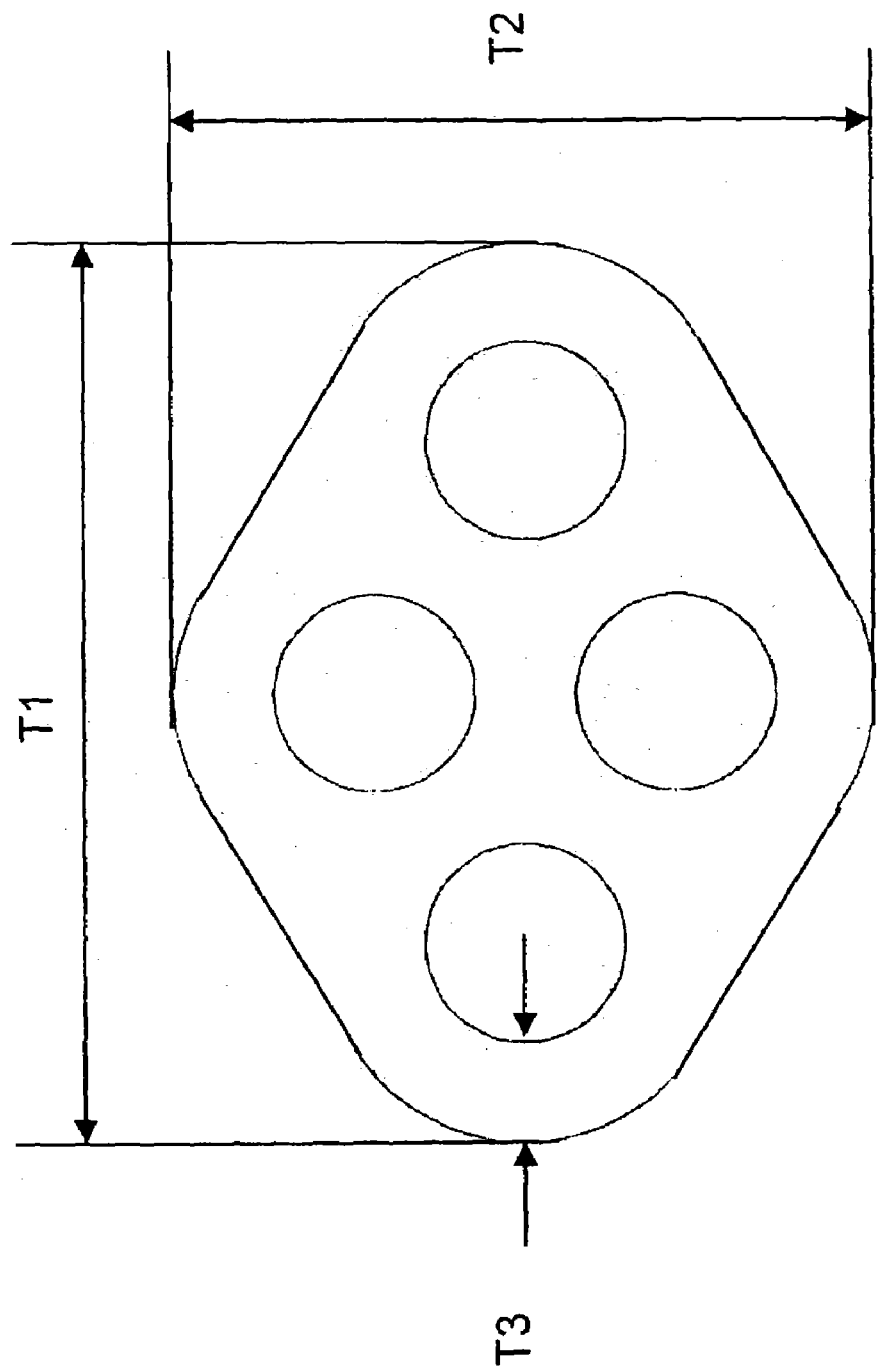
FIG. 4 is a schematic illustration, not to scale, of a catalyst pellet having a rhomboidal cross-section with four circular bores.
Figure 5:
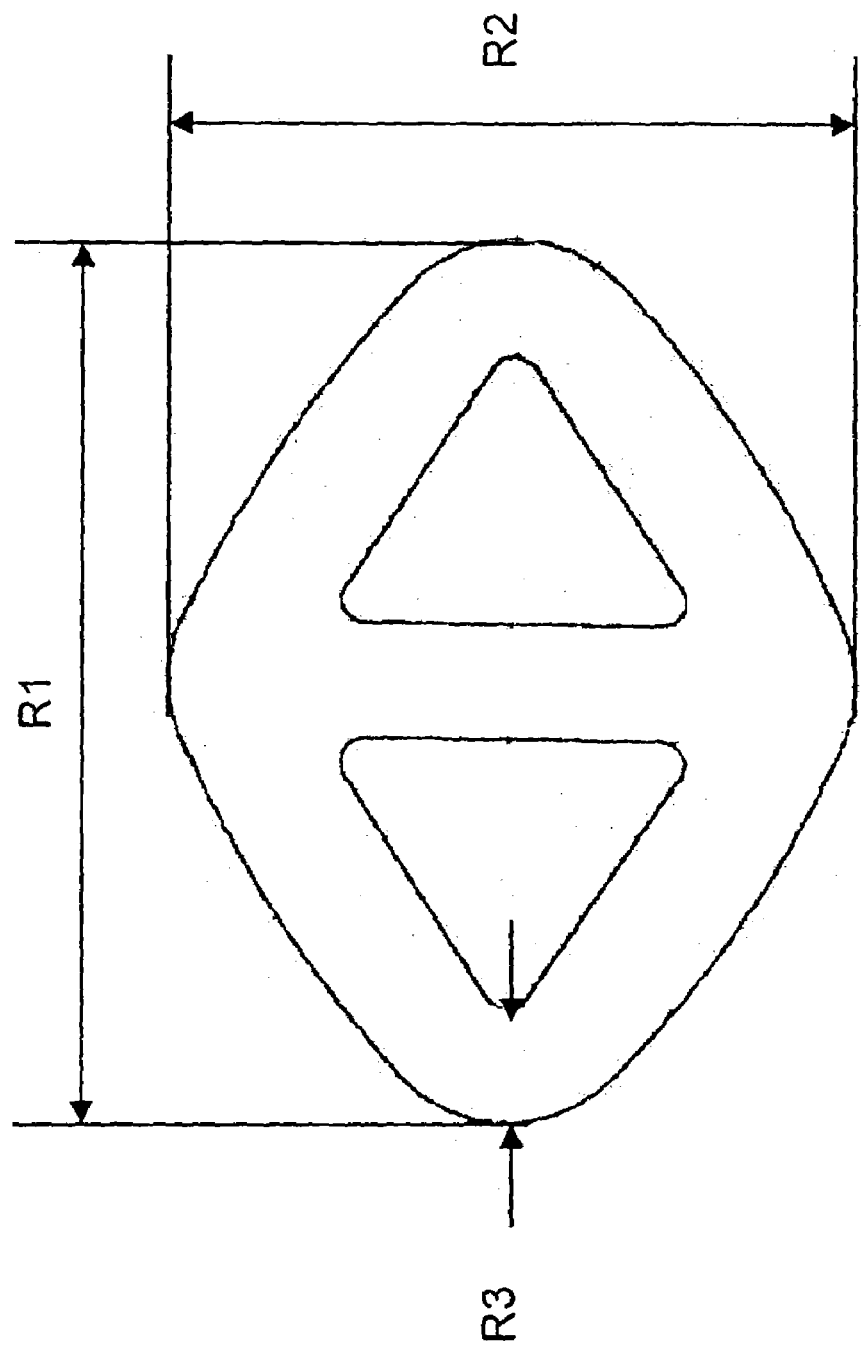
FIG. 5 is a schematic illustration, not to scale, of a catalyst pellet having a rhomboidal cross-section with one reinforcing vane forming two bores and with convex external surfaces.
Figure 6:
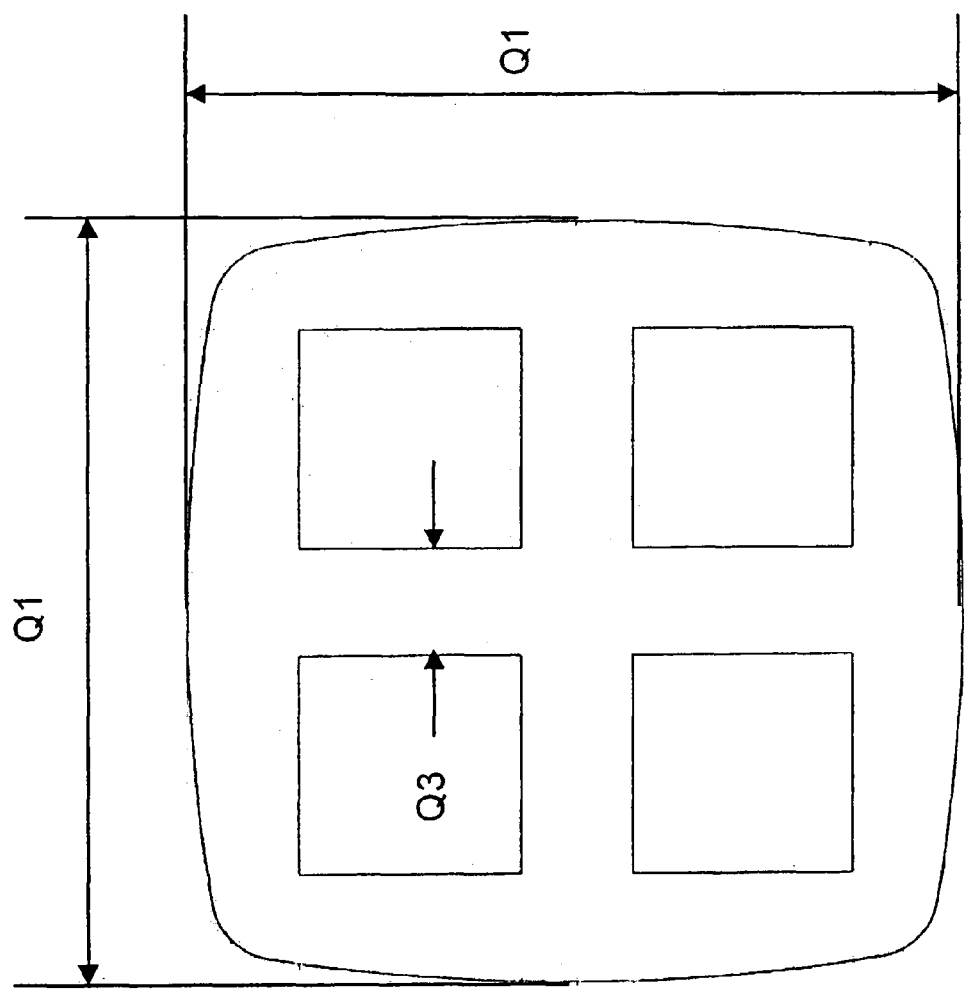
FIG. 6 is a schematic illustration, not to scale, of a catalyst pellet having a square cross-section with two reinforcing vanes forming four bores and with convex external surfaces.
Figure 7:
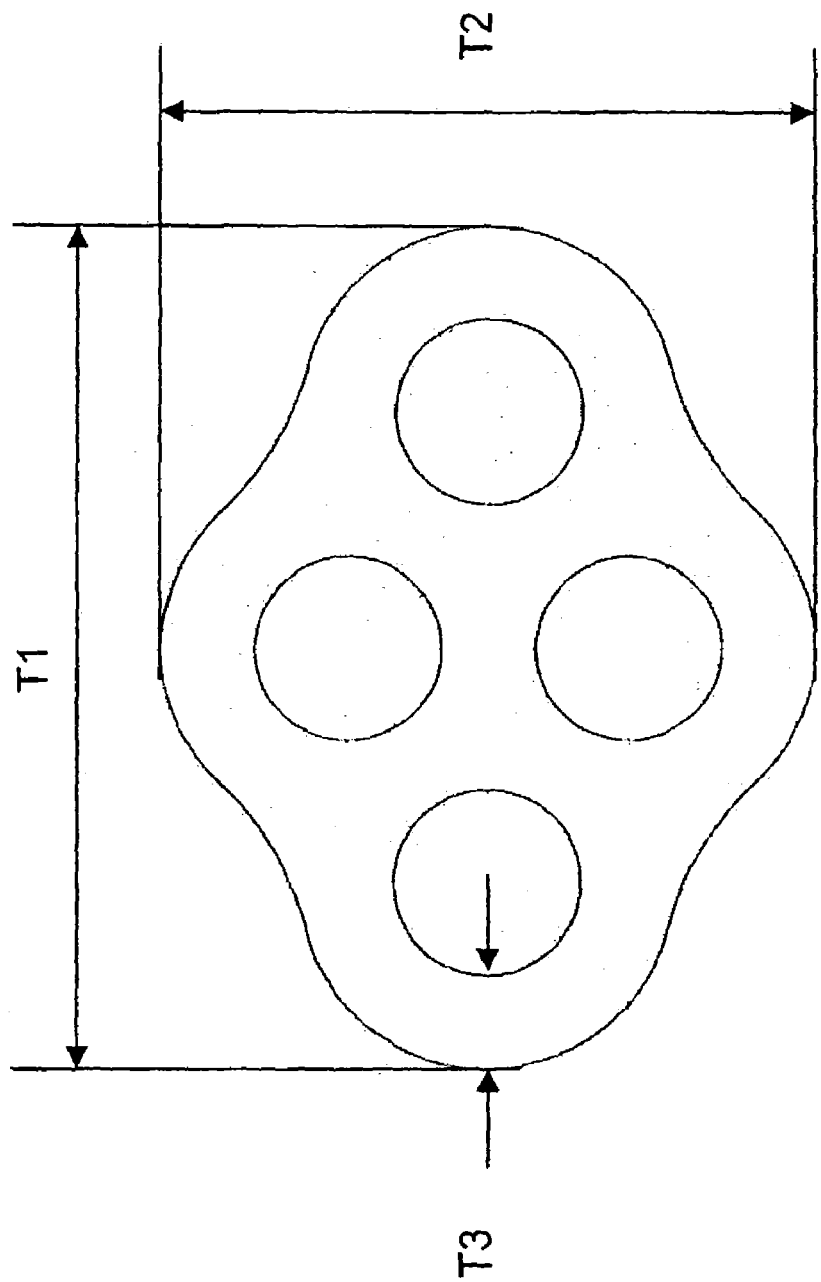
FIG. 7 is a schematic illustration, not to scale, of a catalyst pellet having a rhomboidal cross-section with four circular bores and with concave external surfaces.

Seven different types of catalyst having the shape and size shown in Table 1 and the compositions shown in Table 2 were prepared on the basis of the method described above. In particular, a stearate as a lubricant was added to bohemite and the mixture was moulded into a particle having the shape and size shown in Table 1, by using a tabletting machine. Catalyst A was formed according to the embodiment shown in FIG. 5 of the present invention (catalyst pellet having a rhomboidal cross-section with one reinforcing vane forming two bores and with convex external surfaces), catalyst B according to the embodiment shown in FIG. 6 (catalyst pellet having a square cross-section with two reinforcing vanes forming four bores and with convex external surfaces), catalyst C according to the embodiment shown in FIG. 7 (catalyst pellet having a rhomboidal cross-section with four circular bores and with concave external surfaces). As far as the comparative examples are concerned, catalyst D is a hollow cylinder according to EP 1053789; catalyst E is a hollow cylinder according to U.S. Pat. No. 4,366,093; catalyst F is a hollow cylinder according to U.S. Pat. No. 4,740,644; catalyst G is a hollow cylinder according to U.S. Pat. No. 5,166,120. The carrier pellets were calcined at 823 K for 5 hours, to obtain pellets made of γ-$Al_2O_3$ with the required surface area. The carrier was impregnated by the incipient wetness method with solutions containing a proper concentration of active compounds in order to obtain two types of catalysts with the compositions set out in Table 2.

The reactor loading pattern used, the same for the different types of catalysts tested, was formed of five layers. From the top to the bottom, the layers were as follows: 1) 1200 mm long, containing type I catalyst diluted to 30 vol % with graphite (cylinders with diameter of 5 mm and length of 6.2 mm); 2) 1200 mm long, containing type I catalyst diluted to 40 vol %; 3) 1200 mm long, containing type I catalyst diluted to 60 vol %; 4) 1000 mm long, containing type II catalyst diluted to 45 vol %; 5) 2400 mm long, containing type II catalyst not diluted. The overall catalytic bed was 7 m long.

A large number of tests were carried out comparing mainly the new catalysts of the present invention (A, B, C) with the old hollow cylinder catalysts (D, E, F, G) and the main results are reported in Table 3.

It is evident that all the catalysts of the present invention having a prism-inscribable shape (A, B, C) are superior in the performance, giving the better combination in terms of pressure drop, HCl conversion, selectivity and hot spot temperatures if compared to the hollow cylinder catalysts.

In particular the catalysts A and B show a lower pressure drop than the hollow cylinder ones, because the particular shape increases the void fraction of the related catalytic bed.

It is to underline that, even if the standard hollow cylinder catalyst G has a higher bed void fraction, the measured pressure drop is higher owing to the unavoidable breakage during the loading of this catalyst formed by extrusion.

Furthermore, taking into account that the overall amount in weight of catalyst per unit of volume of reactor tube for the new catalysts A, B, C, is lower than the standard catalysts D, E, F because of the lower bulk density due to the new shapes, we could expect a lower activity per unit volume of reactor tube and therefore a lower HCl conversion for the new catalysts. This is exactly what is obtained with the standard hollow cylinder catalyst G, in comparison with the other hollow cylinder catalysts D, E, F. On the contrary, even if with the new catalysts the overall weight per unit of volume is lower, the HCl conversion is better than the one of the standard catalysts.

The reduced wall thickness of the new catalyst does not imply a reduced mechanical strength, because the new geometry and the well tuned tabletting parameters, allow to maintain an adequate mechanical strength.

Other important results achieved with the new catalysts are the reduced by-product formation, the increase selectivity to EDC and an increased catalyst life.

TABLE 1

| | Catalyst | | | | | | |
|---|---|---|---|---|---|---|---|
| | A | B | C | D | E | F | G |
| $P_1$ main diagonal (mm) | 7.60 | 5.60 | 5.45 | — | — | — | — |
| $P_2$ secondary diagonal (mm) | 5.80 | 5.60 | 3.05 | — | — | — | — |
| $D_e$ external diameter (mm) | — | — | — | 4.90 | 4.90 | 4.90 | 4.90 |
| $D_i$ internal diameter (mm) | — | — | — | 2.25 | 2.25 | 2.00 | 1.30 |
| $P_3$ wall thickness (mm) | 1.00 | 0.80 | 0.60 | 1.32 | 1.32 | 1.45 | 1.80 |
| $P_4$ length (mm) | 6.35 | 6.35 | 6.35 | 6.35 | 5.00 | 5.00 | 9.50 |
| Geometric volume (mm$^3$) | 133 | 117 | 65 | 94 | 74 | 79 | 166 |
| Geometric area (mm$^2$) | 274 | 328 | 210 | 172 | 142 | 140 | 225 |
| S/V (mm$^{-1}$) | 2.06 | 2.80 | 3.21 | 1.82 | 1.91 | 1.78 | 1.35 |
| Bed void fraction | 0.60 | 0.64 | 0.59 | 0.57 | 0.55 | 0.53 | 0.64 |

TABLE 2

| | | Catalyst | | | | | | |
|---|---|---|---|---|---|---|---|---|
| | | A | B | C | D | E | F | G |
| Type I | Carrier | γ-Al$_2$O$_3$ | γ-Al$_2$O$_3$ | γ-Al$_2$O$_3$ | γ-Al$_2$O$_3$ | γ-Al$_2$O$_3$ | γ-Al$_2$O$_3$ | γ-Al$_2$O$_3$ |
| | CuCl$_2$ (%) | 9.5 | 9.5 | 9.5 | 9.5 | 9.5 | 9.5 | 9.5 |
| | KCl (%) | 5.7 | 5.7 | 5.7 | 5.7 | 5.7 | 5.7 | 5.7 |
| | Surface area (m$^2$/g) | 127 | 123 | 125 | 120 | 124 | 125 | 124 |
| | Bulk Density (cm$^3$/g) | 0.65 | 0.58 | 0.67 | 0.69 | 0.73 | 0.76 | 0.55 |
| Type II | Carrier | γ-Al$_2$O$_3$ | γ-Al$_2$O$_3$ | γ-Al$_2$O$_3$ | γ-Al$_2$O$_3$ | γ-Al$_2$O$_3$ | γ-Al$_2$O$_3$ | γ-Al$_2$O$_3$ |
| | CuCl$_2$ (%) | 17.0 | 17.0 | 17.0 | 17.0 | 17.0 | 17.0 | 17.0 |
| | KCl (%) | 1.5 | 1.5 | 1.5 | 1.5 | 1.5 | 1.5 | 1.5 |
| | Surface area (m$^2$/g) | 148 | 150 | 155 | 150 | 155 | 153 | 152 |
| | Bulk Density (cm$^3$/g) | 0.67 | 0.59 | 0.69 | 0.71 | 0.75 | 0.78 | 0.58 |

TABLE 3

| | Catalyst | | | | | | | | | | | |
|---|---|---|---|---|---|---|---|---|---|---|---|---|
| | A | | | B | | | C | | | D | | |
| Trial | 1 | 2 | 3 | 1 | 2 | 3 | 1 | 2 | 3 | 1 | 2 | 3 |
| Inlet temp. (° C.) | 201 | 201 | 201 | 201 | 201 | 201 | 201 | 201 | 201 | 201 | 201 | 201 |
| Outlet temp. (° C.) | 224 | 224 | 224 | 224 | 224 | 224 | 225 | 225 | 225 | 225 | 225 | 225 |
| Hot spot temp. (° C.) | 248 | 248 | 248 | 250 | 250 | 250 | 252 | 252 | 252 | 253 | 253 | 253 |
| Coolant temp. (° C.) | 220 | 220 | 220 | 220 | 220 | 220 | 220 | 220 | 220 | 220 | 220 | 220 |
| Inlet press. (barg) | 6.0 | 6.0 | 6.0 | 6.0 | 6.0 | 6.0 | 6.0 | 6.0 | 6.0 | 6.0 | 6.0 | 6.0 |
| Excess oygen vs HCl | 1.7 | 3.5 | 6.4 | 1.2 | 3.4 | 6.3 | 1.5 | 3.7 | 6.2 | 0.8 | 3.0 | 6.8 |
| Pressure drop (barg) | 1.3 | 1.3 | 1.3 | 1.4 | 1.4 | 1.4 | 2.0 | 2.0 | 2.0 | 1.6 | 1.6 | 1.6 |
| HCl conversion (% mol) | 98.9 | 100 | 100 | 98.8 | 100 | 100 | 99.2 | 100 | 100 | 98.4 | 99.9 | 100 |
| Selectivity to EDC (% mol) | 98.5 | 98.8 | 98.9 | 98.4 | 98.7 | 98.8 | 98.3 | 98.6 | 98.8 | 98.3 | 98.6 | 98.7 |
| Ethyl chloride (% mol) | 0.78 | 0.60 | 0.50 | 0.80 | 0.60 | 0.52 | 0.80 | 0.58 | 0.50 | 0.80 | 0.60 | 0.50 |
| Chlor. by-products (% mol) | 0.44 | 0.28 | 0.23 | 0.50 | 0.36 | 0.28 | 0.58 | 0.47 | 0.30 | 0.58 | 0.43 | 0.38 |
| CO$_x$ (% mol) | 0.28 | 0.32 | 0.37 | 0.30 | 0.34 | 0.40 | 0.32 | 0.35 | 0.40 | 0.32 | 0.37 | 0.42 |

| | Catalyst | | | | | | | | |
|---|---|---|---|---|---|---|---|---|---|
| | E | | | F | | | G | | |
| Trial | 1 | 2 | 3 | 1 | 2 | 3 | 1 | 2 | 3 |
| Inlet temp. (° C.) | 201 | 201 | 201 | 201 | 201 | 201 | 201 | 201 | 201 |
| Outlet temp. (° C.) | 226 | 226 | 226 | 228 | 228 | 228 | 230 | 230 | 230 |
| Hot spot temp. (° C.) | 256 | 256 | 256 | 260 | 260 | 260 | 251 | 251 | 251 |
| Coolant temp. (° C.) | 220 | 220 | 220 | 220 | 220 | 220 | 220 | 220 | 220 |
| Inlet press. (barg) | 6.0 | 6.0 | 6.0 | 6.0 | 6.0 | 6.0 | 6.0 | 6.0 | 6.0 |
| Excess oygen vs HCl | 2.0 | 6.3 | | 2.9 | 4.4 | 6.1 | 1.5 | 3.5 | 6.5 |
| Pressure drop (barg) | 1.8 | 1.8 | 1.8 | 2.0 | 2.0 | 2.0 | 1.8 | 1.8 | 1.8 |
| HCl conversion (% mol) | 98.5 | 99.8 | 100 | 98.4 | 99.1 | 99.6 | 97.9 | 98.4 | 99.5 |
| Selectivity to EDC (% mol) | 98.2 | 98.4 | 98.5 | 98.0 | 98.2 | 98.4 | 98.2 | 98.5 | 98.6 |
| Ethyl chloride (% mol) | 0.80 | 0.60 | 0.55 | 0.74 | 0.65 | 0.55 | 0.85 | 0.65 | 0.56 |
| Chlor. by-products (% mol) | 0.69 | 0.65 | 0.55 | 1.06 | 0.83 | 0.66 | 0.55 | 0.40 | 0.35 |
| CO$_x$ (% mol) | 0.31 | 0.35 | 0.40 | 0.30 | 0.32 | 0.39 | 0.40 | 0.45 | 0.49 |

The invention claimed is:

1. A method for selectively catalyzing gas phase exothermic reactions comprising employing in said reaction a catalyst pellet comprising:
   a. a uniform cross-section or, if not uniform, a cross section having a deviation from the average cross-section area of less than 30%, wherein the cross-section is substantially parallelogram-shaped; and
   b. one or more through-bores, having:
      1. axes which are parallel to each other and to the axis of the pellet or, if not parallel, axes having a deviation from a parallel line of less than 20%; and
      2. uniform cross-sections, or, if not uniform, cross-sections having a deviation from the average cross-section of less than 30%; and wherein said one or more through-bores further comprise:
         i. one bore having the same shape as the cross-section of the pellet or two or more bores obtained by introducing internal reinforcing vanes in said one bore; or
         ii. two or more bores having a circular or elliptical shape and, if four or more bores are present, having different distances between the centres of the non-adjacent couples of bores.

2. A method according to claim 1 wherein the catalyst pellet has the following size: 4 mm<$P_1$<15 mm, 4 mm<$P_2$<15 mm, 0.5 mm<$P_3$<4 mm, 3 mm<$P_4$<15 mm; wherein $P_1$ is the main diagonal of the parallelogram, $P_2$ is the secondary diagonal of the parallelogram, $P_3$ is the maximum wall thickness, and $P_4$ is the length of the parallelogram.

3. A method according to claim 2 wherein the catalyst pellet has the following size: 4 mm<$P_1$<9 mm, 4 mm<$P_2$<9 mm, 0.7 mm<$P_3$<2 mm, 4 mm<$P_4$<8 mm.

4. A method according to claim 1 wherein the catalyst pellet has a rhomboidal cross-section with at least one reinforcing vane connecting two opposite edges and at least two bores.

5. A method according to claim 4 wherein the catalyst pellet has the following size: 4 mm<$R_1$<15 mm, 4 mm<$R_2$<15 mm, 0.5 mm<$R_3$<3 mm, 3 mm<$R_4$<15 mm; wherein $R_1$ is the longest size of the cross-section, $R_2$ is the shortest size of the cross-section, $R_3$ is the largest wall thickness of the bores, and $R_4$ is the length.

6. A method according to claim 5 wherein the catalyst pellet has the following size: 4 mm<$R_1$<9 mm, 4 mm<$R_2$<9 mm, 0.7 mm<$R_3$<2 mm, 4 mm<$R_4$<8 mm.

7. A method according to claim 1 wherein the catalyst pellet has a rhomboidal cross-section with at least one reinforcing vane connecting two opposite sides and at least two bores.

8. A method according to claim 7 wherein the catalyst pellet has the following size: 4 mm<$R_1$<15 mm, 4 mm<$R_2$<15 mm, 0.5 mm<$R_3$<3 mm, 3 mm<$R_4$<15 mm; wherein $R_1$ is the longest size of the cross-section, $R_2$ is the shortest size of the cross-section, $R_3$ is the largest wall thickness of the bores, and $R_4$ is the length.

9. A method according to claim 8 wherein the catalyst pellet has the following size: 4 mm<$R_1$<9 mm, 4 mm<$R_2$<9 mm, 0.7 mm<$R_3$<2 mm, 4 mm<$R_4$<8 mm.

10. A method according to claim 7 wherein the catalyst pellet has a square cross-section with at least two reinforcing vanes and four bores.

11. A method according to claim 10 wherein the catalyst pellet has the following size: 3 mm<$Q_1$<10.5 mm, 0.5 mm<$Q_3$<3 mm, 3 mm<$Q_4$<15 mm; wherein $Q_1$ is the side of the square, $Q_3$ is the wall thickness, and $Q_4$ is the length.

12. A method according to claim 11 wherein the catalyst pellet has the following size: 4 mm<$Q_1$<9 mm, 0.7 mm<$Q_3$<2 mm, 3 mm<$Q_4$<8 mm.

13. A method according to claim 1 wherein the catalyst pellet has a rhomboidal cross-section with at least four circular bores.

14. A method according to claim 13 wherein the catalyst pellet has the following size: 4 mm<$T_1$<15 mm, 4 mm<$T_2$<15 mm, 0.5 mm<$T_3$<3 mm, 3 mm<$T_4$<15 mm; wherein $T_1$ is the longest size of the cross-section, $T_2$ is the shortest size of the cross-section, $T_3$ is the largest wall thickness of the bores, and $T_4$ is the length; and wherein the diameter of the bores is between 0.7 and 3 mm.

15. A method according to claim 14 wherein the catalyst pellet has the following size: 4 mm<$T_1$<9 mm, 4 mm<$T_2$<9 mm, 0.7 mm<$T_3$<2 mm, 3 mm<$T_4$<8 mm.

16. A method according to claim 1 wherein the sides and/or the corners of the external contour of the catalyst pellet cross-section are rounded in such a way that the catalyst pellet cross-section remains substantially parallelogram-shaped and the ratio between the area of the cross-section of the pellets, including the cross-section of the bores, and the area of the parallelogram circumscribing the external contour of the pellet cross-section is greater than 0.75.

17. A method according to claim 16 wherein said ratio is greater than 0.85.

18. A method according to claim 1 wherein the sides of the external contour of the catalyst pellet cross-section are curved, the curve being convex or concave or both.

19. A method according to claim 18 wherein the curve is convex.

20. A method according to claim 1 wherein the sides and/or the edges of the external contour of the catalyst pellet cross-section are curved, and the curves corresponding to the sides of the external contour of the cross-section are concave and the curves corresponding to the edges of the external contour of the cross-section are convex.

21. A method according to claim 1 with one bore having the same shape as the cross-section of the catalyst pellet or, optionally, with two or more bores obtained by introducing internal reinforcing vanes in said one bore, wherein the sides and/or the corners of the contour of the bores cross-section are rounded in such a way that the ratio between the area of the cross-section of the bores and the area of the cross-section of the parallelogram circumscribing the external contour of the bores is higher than 0.75.

22. A method according to claim 21 wherein said ratio is higher than 0.85.

23. A method according to claim 1 wherein the catalyst pellet has two or more bores obtained by introducing internal reinforcing vanes in one bore having the same shape of the cross-section of the pellet, wherein said reinforcing vanes are disposed to connect the opposite edges or the opposite sides of the external contour of the bore cross-section.

24. The method of claim 1 wherein the gas phase exothermic reaction is selected from the group consisting of selective chlorination and/or oxychlorination of alkenes or alkanes, and the selective oxidation of alkenes.

25. The method of claim 24, wherein the gas phase exothermic reaction is selected from the group consisting of: the conversion of ethylene with chlorine to 1,2-dichloroethane; the conversion of ethylene with hydrogen chloride with air or oxygen to give 1,2-dichloroethane; the conversion of ethane with hydrogen chloride with air or oxygen to give saturated and unsaturated chlorinated hydrocarbons; and the reaction of methane with chlorine.

26. The method of claim 25, wherein the gas phase exothermic reaction is the oxychlorination of ethylene and the catalyst pellet contains copper in an amount of 1–12 wt %.

27. The method of claim 25, wherein the gas phase exothermic reaction is the oxychlorination of ethane and the catalyst pellet contains copper and/or nickel and an alkali metal.

28. The method of claim 27, wherein the catalyst pellet further comprises at least one of the alkaline earth metals, group IIB metals or lanthanides.

29. The method of claim 25, wherein the gas phase exothermic reaction is the selective oxidation of ethylene and the catalyst pellet further comprises silver and at least one of the alkali or alkaline earth metals.

30. The method of claim 26, wherein the catalyst pellet further comprises at least one of the alkali metals, alkaline earth metals, group IIB metals or lanthanides in a total amount up to 15 wt %.

31. The method of claim 30, wherein the alkali metal is lithium, potassium, cesium, or combinations thereof.

32. The method of claim 30, wherein the alkaline earth metal is magnesium.

33. The method of claim 30, wherein the lanthanide is cerium, lanthanum, or a combination thereof.

34. A method for selectively catalyzing gas phase endothermic reactions comprising employing in said reaction a catalyst pellet comprising:
   a. a uniform cross-section or, if not uniform, a cross section having a deviation from the average cross-section area of less than 30%, wherein the cross-section is substantially parallelogram-shaped; and
   b. one or more through-bores, having:
      1. axes which are parallel to each other and to the axis of the pellet or, if not parallel, axes having a deviation from a parallel line of less than 20%; and
      2. uniform cross-sections, or, if not uniform, cross-sections having a deviation from the average cross-section of less than 30%; and wherein said one or more through-bores further comprise:
         i. one bore having the same shape as the cross-section of the pellet or two or more bores obtained by introducing internal reinforcing vanes in said one bore; or
         ii. two or more bores having a circular or elliptical shape and, if four or more bores are present, having different distances between the centres of the non-adjacent couples of bores.

* * * * *